United States Patent
Yeandel et al.

(10) Patent No.: US 8,128,604 B2
(45) Date of Patent: Mar. 6, 2012

(54) DEVICE AND METHOD FOR DOSING A SUBSTANCE

(75) Inventors: Julian Yeandel, Thun (CH); Stefan Jost, Muehleberg (CH); Beat Steffen, Saanen (CH)

(73) Assignee: TecPharma Licensing AG, Burgdorf (CH)

( * ) Notice: Subject to any disclaimer, the term of this patent is extended or adjusted under 35 U.S.C. 154(b) by 1701 days.

(21) Appl. No.: 11/009,387

(22) Filed: Dec. 10, 2004

(65) Prior Publication Data

US 2005/0182360 A1  Aug. 18, 2005

Related U.S. Application Data

(63) Continuation of application No. PCT/CH03/00359, filed on Jun. 5, 2003.

(30) Foreign Application Priority Data

Jun. 10, 2002 (DE) .................................. 102 25 707

(51) Int. Cl.
*A61M 5/00* (2006.01)

(52) U.S. Cl. ........................................ 604/232; 604/208
(58) Field of Classification Search ............... 604/96.01, 604/207–211, 232–234, 151–155, 218–231
See application file for complete search history.

(56) References Cited

U.S. PATENT DOCUMENTS 5,383,865 A * 1/1995 Michel .......................... 604/232
5,509,905 A * 4/1996 Michel .......................... 604/207
2004/0207385 A1 10/2004 Gafner

FOREIGN PATENT DOCUMENTS

| | | |
|---|---|---|
| DE | 101 33 216 A1 | 1/2003 |
| EP | 0 554 996 | 8/1993 |
| EP | 0 581 925 B1 | 11/1995 |
| EP | 1 095 668 | 5/2001 |
| FR | 2 799 858 | 4/2001 |
| WO | 97/01362 | 1/1997 |

OTHER PUBLICATIONS

Related PCT International Search Report.

* cited by examiner

*Primary Examiner* — Kevin C Sirmons
*Assistant Examiner* — Phillip Gray
(74) *Attorney, Agent, or Firm* — Dorsey & Whitney LLP; David E. Bruhn, Esq.

(57) ABSTRACT

A device for dosing a substance, including at least one rotating element and at least one coding element associated with the rotating element, using which the rotational position of the rotating element can be identified, further including at least one reference element whereby a reference signal is generated at pre-set positions or changes in position, and a method for identifying the rotational position of a rotating element which serves to set a dose, wherein the rotational position of the rotating element is identified by a coding which is only read or evaluated when a reference signal is generated at pre-set rotational positions or positional transitions.

19 Claims, 8 Drawing Sheets

Section B-B

Section A-A

Section C-C

Section D-D

DEVICE AND METHOD FOR DOSING A SUBSTANCE

CROSS-REFERENCE TO RELATED APPLICATION(S)

This application is a continuation of International Application No. PCT/CH03/00359, filed on Jun. 5, 2003, which claims priority to German Application No. 102 25 707.8, filed on Jun. 10, 2002, the contents of which are incorporated herein in their entirety by reference.

BACKGROUND

The present invention relates to devices and methods for dispensing, delivering or administering substances, including, in one embodiment, a device and a method for dosing or dispensing a preferably injectable substance in doses or selected amounts from an injection or infusion device. More particularly, the present invention relates to a device and a method for setting and/or measuring a dispensed dosage of a substance or a dosage of the substance to be dispensed.

EP 0 581 925 B1 and corresponding U.S. Pat. No. 5,509,905, the disclosures and teachings of which are incorporated herein by reference, disclose an injection apparatus comprising an operating button using which switching means can be operated which engage with a switch piece wherein they operate switches, wherein the number of partial rotations of the operating button is indicated on a indicating means and an axial movement of the operating button can only be performed at the end of such a partial rotation. While this ensures that the operating button is operated in a defined way, errors may occur when setting a dosage.

In general, setting a dosage to be dispensed needs to be performed exactly. It is also preferable that the setting be monitored, and any errors occurring during the setting procedure should be recognized.

In order to code four rotational positions, coding the four positions using a Gray code is for example known, as shown in FIG. 4, such that in the two-digit binary code shown, the coding of neighbouring positions differs only by changing a single bit. If, for example, an error occurs in the second bit, such that it remains constantly set to zero, the transition from Position A to Position B is not recognized by the value "00" which then remains unchanged, and the subsequent transition from Position B to Position C with the erroneous code "10" is erroneously interpreted as a transition from Position A to Position B (coding: 00 to coding: 10), such that the rotational direction is incorrectly interpreted.

If four rotational positions A to D with four intermediate states resulting from changes in state are coded using three bits, as shown in FIG. 5, then the rotational direction can for example be incorrectly interpreted if the first bit erroneously remains at the value 0. A transition from the intermediate state bc (coding: 001) to Position C (correct coding: 101; erroneous coding: 001) is not recognized. A subsequent transition to the intermediate state cd (correct coding: 111; erroneous coding: 011) is interpreted as a transition from the intermediate state bc to Position B.

Thus, through a single erroneous bit, the exemplary codings shown in FIGS. 4 and 5 can result in a rotational direction opposite to the actual rotational direction being determined. Thus, for example, an increase in a set dosage may be erroneously interpreted as a reduction in the dosage amount and, for example, a warning erroneously may not be output or signalled when a dosage is set too high.

SUMMARY

An object of the present invention is to provide for identifying the rotational position of a rotating element.

In one embodiment, the present invention comprises a device comprising at least one rotating element, at least one coding element and a reference element, whereby the rotational position of the rotating element can be identified.

In one embodiment, the present invention comprises a device comprising at least one rotating element, at least one coding element and a reference element, whereby the rotational position of the rotating element can be identified, and whereby a reference signal is generated at pre-set positions or changes in position of the rotating element.

In one embodiment, the present invention comprises a method for identifying the rotational position of a rotating element, wherein the rotational position of the rotating element is identified by a coding which is read or evaluated.

In one embodiment, the present invention comprises a method for identifying the rotational position of a rotating element, wherein the rotational position of the rotating element is identified by a coding which is read or evaluated when a reference signal is generated at pre-set rotational positions or positional transitions.

In one embodiment, the device in accordance with the invention can be contained in or associated with an infusion or injection apparatus, wherein a moving, e.g., rotating, element is provided and the amount of a substance to be dispensed, or the amount of a substance dispensed, is set or measured using the position, e.g., the rotational position, of said moving element. Thus, in one embodiment, the present invention comprises an infusion or injection apparatus for dispensing, administering or dosing a selected amount of a substance.

It is an object of the present invention to provide a device and a method whereby a dispensed dose or amount dependent on a rotational position of an element of the device can be detected reliably and without error. It is also an object of the present invention to provide a device and a method whereby a dose or amount to be dispensed dependent on a rotational position of an element of the device can be detected reliably and without error.

It is an object of the present invention to provide a device and a method using which a rotational position, and therefore a dispensed dosage or dosage to be dispensed dependent on the rotational position of an element, can be detected reliably and without error.

Conventionally, in an injection apparatus, once the dosage or amount of the substance to be dispensed has been set, the substance is dispensed by pressing on a triggering element which is often also the setting element. At least one coding element is provided on the rotating element, which enables the rotational position to be detected, wherein the coding is, for example, configured such that four different rotational positions, each offset by 90° with respect to the respectively neighbouring position, can be detected. In general, two, three, five or more rotational positions can also be differentiated by the coding, depending on the number of differentiating elements or bits available and the coding chosen, such that, for example, eight rotational positions can also be differentiated from each other.

In accordance with one embodiment of the present invention, rotational positions can be either determined positions and/or rotational angles or angular ranges, i.e., such that, for example, rotating the rotating element by 85° to 95° from an initial position is detected as a quarter rotation with a tolerance range of 5°. In accordance with one embodiment, at least one reference element is provided which can, for example, be attached to or integrated into the rotating element or is separate from the rotating element and can co-operate with an element or partial piece of the rotating element, wherein the reference element only generates a signal in at least one and, in some embodiments, preferably two, three, four or more pre-set positions. The reference element can also, for example, be configured such that a signal is generated in an initial state of the rotating element and at every rotational position offset by a multiple of 90° from said initial state, such that a signal is generated at a rotation of 0°, 0°, 180°, 270° and 360° in each direction.

In general, the reference element in accordance with one embodiment of the present invention can also be used with other movements, such as, for example, a longitudinal or linear movement, in order to generate corresponding reference signals.

In some embodiments, the reference element is preferably configured such that a reference signal is only generated when the rotating element is positioned as exactly as possible, i.e., no deviation or only a very small deviation of, for example, up to 1° from the respective position is tolerated, in order to output the reference signal. Alternatively, a larger tolerance range can also be pre-set which allows the rotational position of the rotating element to deviate from a pre-set position by, for example, up to 10° or up to 30° or 45°, in order to generate the reference signal.

It is equally possible, in some embodiments, using the reference element, to only generate a reference signal for pre-set changes in position, i.e., for example, before and/or after a defined position or defined state.

Using the reference element in accordance with some embodiments of the present invention, a reference signal can thus be generated which can be used to read a coding for ascertaining the rotational position of the rotating element, only at pre-set defined rotational positions, so as to achieve greater reliability when coding and/or reading a coding and thus to recognize errors or to reject errors occurring in intermediate states. If, for example, the elements provided for coding the rotational state are arranged such that undefined or incorrect codes indicating a rotational position which does not correspond to the actual rotational position can occur in the case of intermediate positions which deviate from pre-set rotational positions having defined codes, then the reference element in accordance with the invention can exclude the possibility that such intermediate states are detected and interpreted as errors or incorrect rotational positions which do not correspond to an actual rotational position of the rotational element.

In some preferred embodiments, the at least one reference element for generating at least one reference signal is formed such that it can not only recognize but also correct errors. Thus, for example, a coding comprising pre-set valid codes or states can be chosen, with which an erroneous bit can be recognized and corrected. To this end, the codes should exhibit a sufficient gap from each other.

In some preferred embodiments, the reference signal can also be used to switch on and/or off power-consuming elements such as, for example, the electronic system of an infusion apparatus. For example, the electronic system may only be activated when the reference element indicates that a relevant change in position has occurred, such that power is not consumed in intermediate states which are not of interest.

In some embodiments, the coding elements which serve to identify or recognize the rotational position and/or the reference element can advantageously be formed as mechanical elements, as shown by way of example in FIGS. 1 to 3. A two-digit or multiple-digit code for coding a rotational position can, for example, be generated by a rotational body which comprises a disc element for each individual bit which comprises a protruding element in accordance with the respective rotational position, in order to press a neighbouring switch at a particular rotational position and so establish a contact. At a different rotational position, no protruding element is provided, such that a neighbouring switch is not pressed. The individual discs assigned to the respective bits can comprise protruding elements at positions offset or rotated with respect to each other, such that a multiple-digit coding can be realized, wherein the individual bits can be changed independently of each other, in accordance with the respective rotational position.

In some embodiments of the present invention, the elements which serve for coding and/or the at least one reference element can be based on optical principles, i.e., can, for example, be light barriers or photodiodes which detect emitted light signals and can recognize a presence or interruption of light signals using corresponding light-emitting or reflective elements which serve for coding or referencing. Optical elements enable non-contact scanning and can be used over a longer period of time due to the substantial absence of wear as compared to mechanical elements.

Furthermore, in some embodiments, it is possible to configure the coding elements and/or the reference element capacitively and/or inductively, as is, for example, described in the German patent application having the application number 101 33 216.5 and the corresponding U.S. Patent Application US 2004/0207385, the disclosures of which with respect to the configuration of capacitive elements are incorporated into this application.

In some embodiments, it is possible to realize the coding elements and/or the reference element using a combination of the variants described above, for example coding the rotational position may be realized using mechanical elements, while the reference element is realized using optical elements.

In some embodiments, the code used to code the rotational position can advantageously be a Gray code, wherein it is possible to provide a coding with two, three, four or more bits, in order to code the desired number of different rotational positions.

In some embodiments, an indicating element is advantageously provided on an infusion or injection apparatus in accordance with the present invention in order to indicate a rotational position detected by the coding and the reference element and/or a corresponding dosage amount set or dispensed and to draw attention to any errors in coding. In some preferred embodiments, a reset switch can also be provided which can be separately operated in order to, for example, introduce a new measuring or dosing procedure.

In accordance with another aspect of the present invention, the present invention relates to a method for setting and/or measuring a dosage or amount of a dispensed substance or a substance to be dispensed, wherein a two-digit or multiple-digit code is only read or evaluated for positions or changes in position pre-set by a reference element. Erroneous codings from non-defined intermediate states cannot then result in erroneously recognizing an actual rotational position.

In one embodiment of the method in accordance with the invention, an occurring error is advantageously recognized, for example by pre-setting permissible transitions from pre-set coding states and/or permissible codes and comparing actually detected codes and changes in coding with the permissible codings and changes in code.

BRIEF DESCRIPTION OF THE DRAWINGS

FIG. 3, including

DETAILED DESCRIPTION

Figure 1:
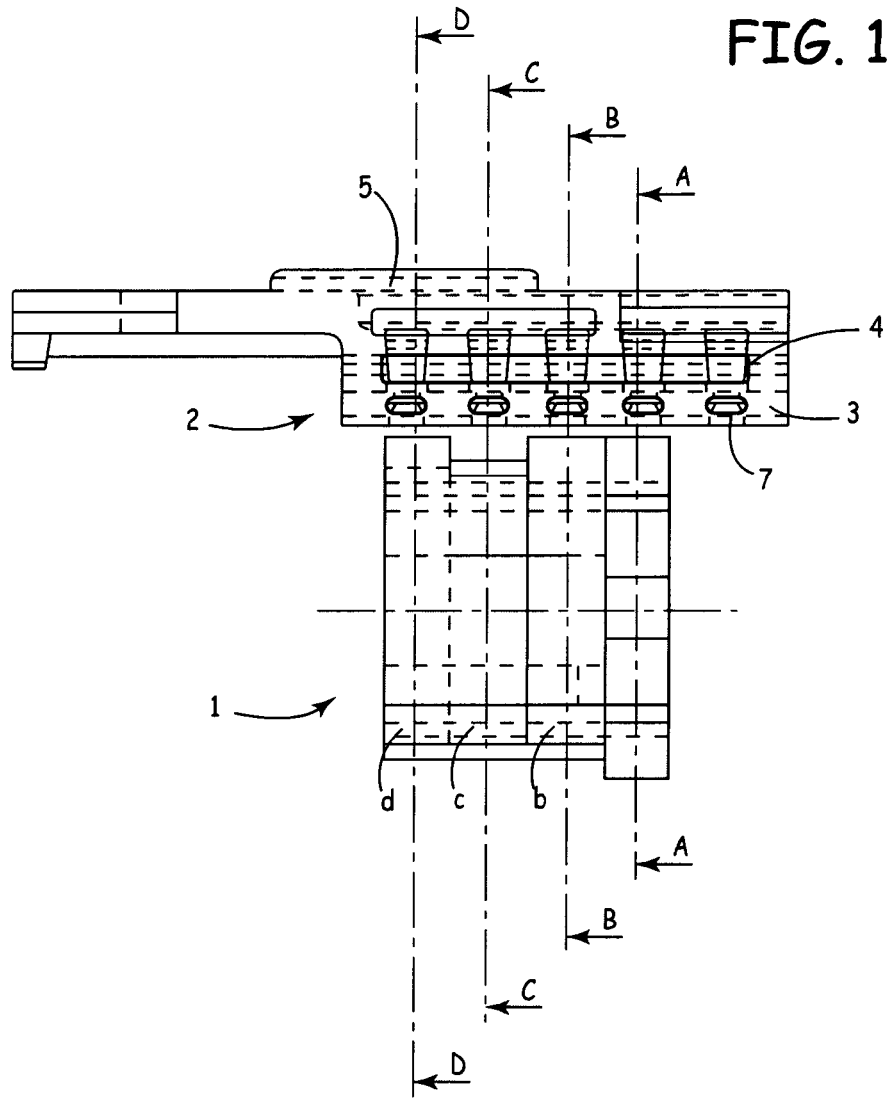
FIG. 1 is a side view of a mechanical embodiment of an element in accordance with one embodiment of the present invention for setting a dosage of an infusion device, with an assigned switching array.

FIG. 1 shows a rotating element provided as a cam shaft 1 which is opposed by a coding element provided as a power consuming switching and electronics element 2 when installed in an infusion apparatus, wherein the four cams of the cam shaft 1, represented by the respective cross-sections AA to DD (see also FIG. 3, including respective FIGS. 3a-d), each oppose a switching element of a switching pad 3 which is pressed onto a circuit board 4 in accordance with the rotational position of the cam shaft 1, in order to establish an electrical contact. An indicator 5 is provided on the upper side of the switching and electronics element 2 and can indicate a rotational position of an element (not shown) connected to the cam shaft 1, for example pushed through it, and/or a corresponding dosage set, in accordance with the coding determined by the cam shaft 1.

Figure 2:
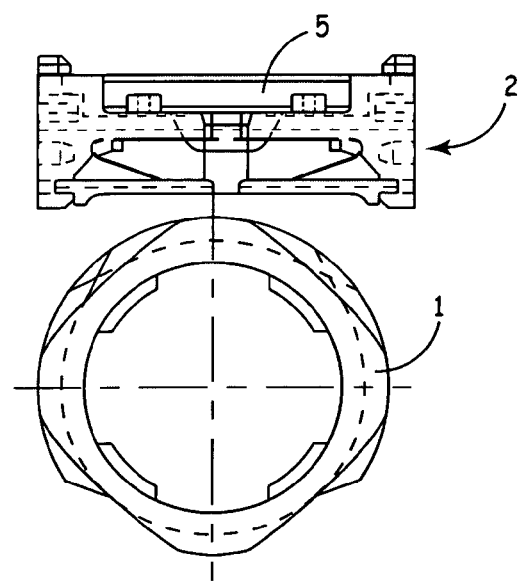
FIG. 2 depicts the device shown in FIG. 1, in a top view.

FIG. 2 shows the array shown in FIG. 1, in a top view, wherein it may be seen that the cam shaft 1 comprises four protrusions, each offset by 90° with respect to each other, on its inner side, such that the cam shaft 1 can be pushed, secured against rotating, onto a setting and pressing button (not shown), in order to enable a dosage to be set by rotating the button and the set dosage to then be dispensed by pressing on the button while simultaneously pushing the button through the cam shaft 1.

Figure 3B:
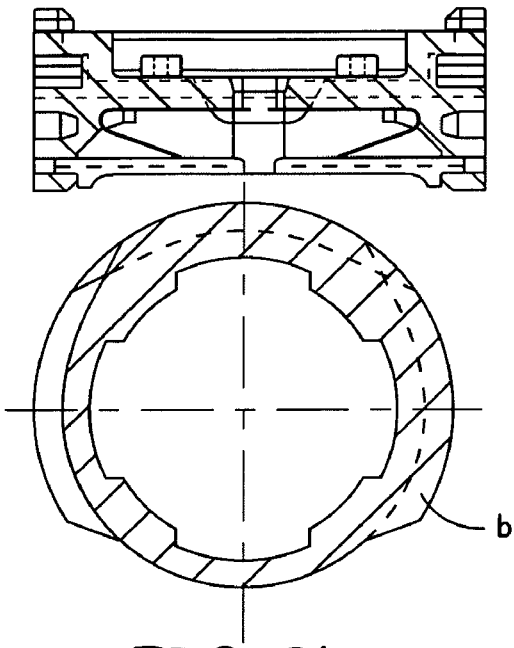
FIGS. 3a-d, depicts cross-sections at the positions indicated in FIG. 1.
Figure 3A:
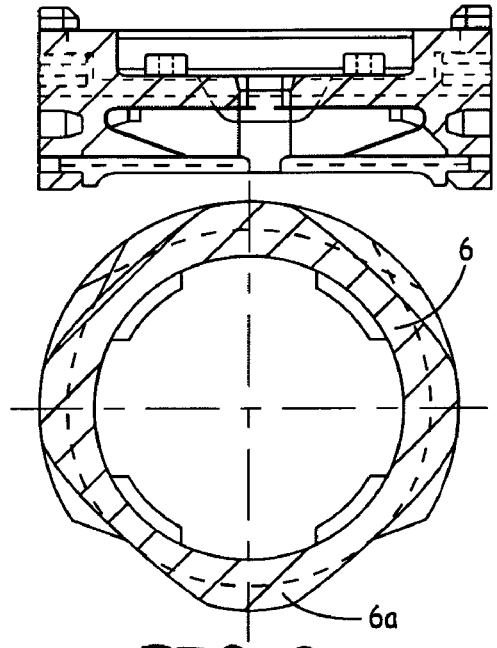

FIG. 3, including FIGS. 3a-d, shows the cross-sectional views AA to DD indicated in FIG. 1, wherein FIG. 3a (section A-A) shows, in cross-section, a reference element 6 in accordance with one embodiment of the present invention comprising four protrusions 6a offset by 90° with respect to each other and which only establish a contact at the assigned switching element of the switching pad 3 in four rotational positions of the cam shaft 1 to generate a reference signal, each offset by 90° with respect to each other, in order to read a code generated by the other partial elements of the cam shaft 1 only at these defined reference positions.

Figure 3C:
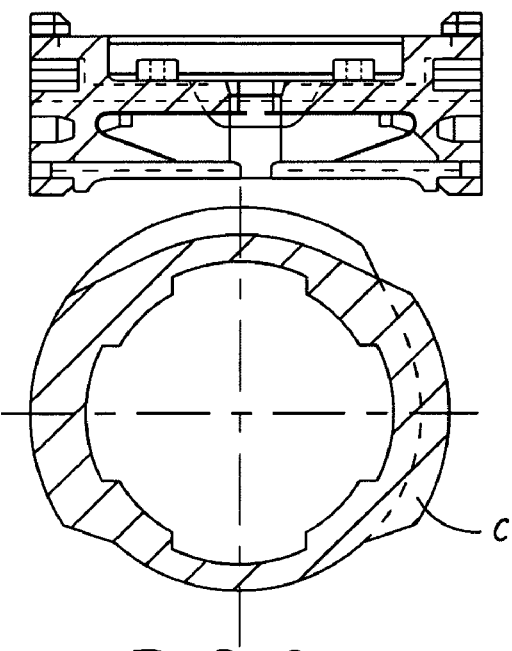
Figure 3D:
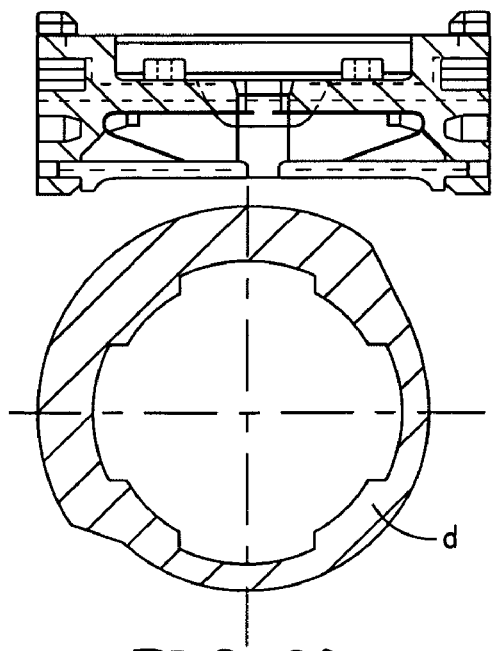
Figure 4:
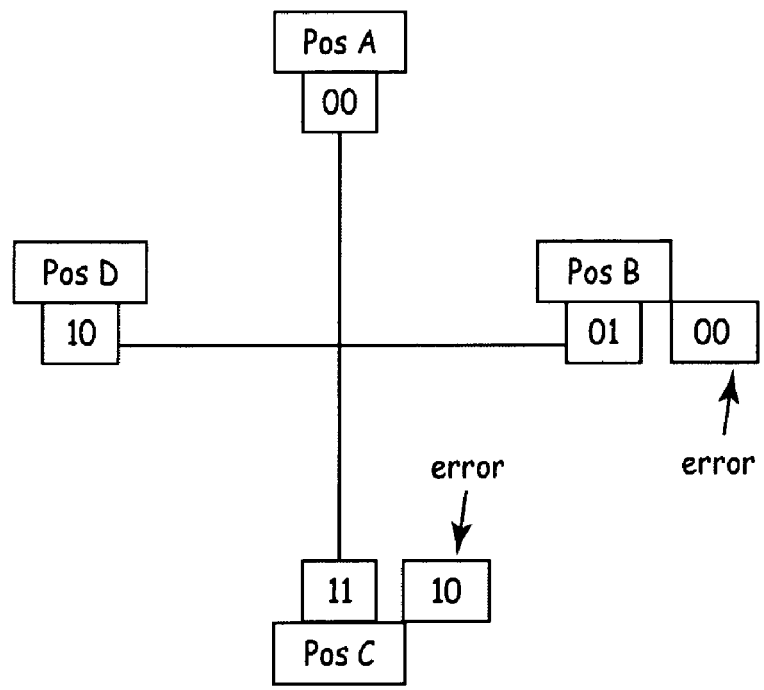
FIGS. 4 and 5 depicts known codings of rotational positions using two and three bits.
Figure 5:
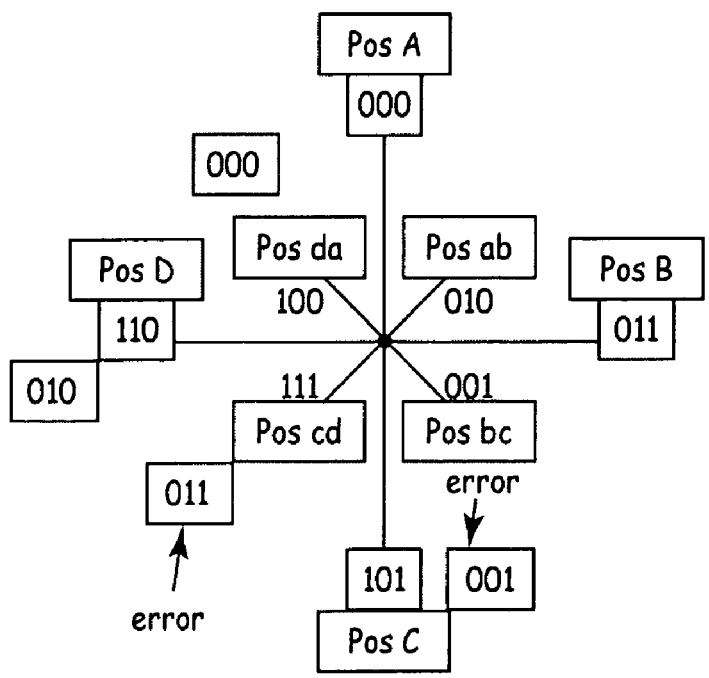

FIGS. 3b-d (sections BB to DD) show the other partial elements of the cam shaft 1, provided for realising a three-digit coding, and using which differnet codes can be generated in accordance with the rotational position of the cam shaft 1. The position shown in FIG. 3, for example, is coded as "101" if a switching element being pressed corresponds to the state "1" and a code is determined in the order sections of BB to DD.

If the cam shaft 1 is rotated further, clockwise from the position shown in FIG. 3, then firstly the corresponding switching connection is interrupted by the reference element 6 and not closed again until the cam shaft 1 has rotated further by about 90°, in order to indicate that the code is a valid code. Starting from the rotational position shown in FIG. 3, the position rotated by 90° clockwise is coded by the code "011".

Figure 6:
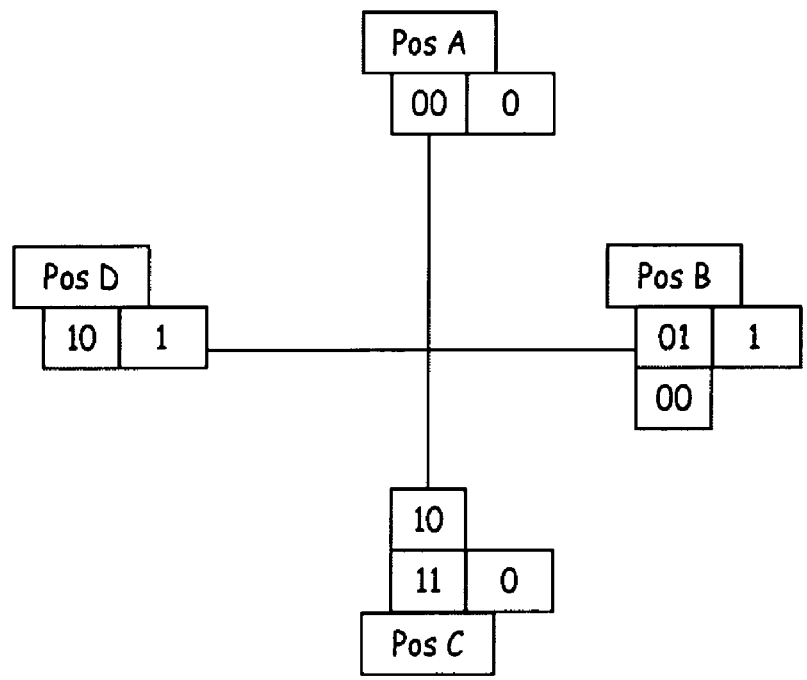
FIG. 6 depicts a two-bit Gray coding comprising a reference bit in accordance with one embodiment of the present invention for indicating transitions.

FIG. 6 shows four rotational position being coded using a two-digit Gray code and a reference bit which indicates positional transitions. If, for example, it is assumed that the second bit erroneously remains at "0", then a transition from Position A to Position B is not recognized if only the first two bits are considered. If, however, the additional third reference bit is considered in accordance with one embodiment of the present invention, then it can be determined from the change in the reference bit that a positional transition has occurred and the code "001" is outputted. Because this code "001" is not provided, it can be determined that an error has occurred. The subsequent transition from Position B to Position C generates the code "100", which can also be recognized as invalid and thus draws attention to the fact that an error has occurred. Thus, the additional reference bit can be used both to indicate a change in position and to check the accuracy of a code.

Figure 7:
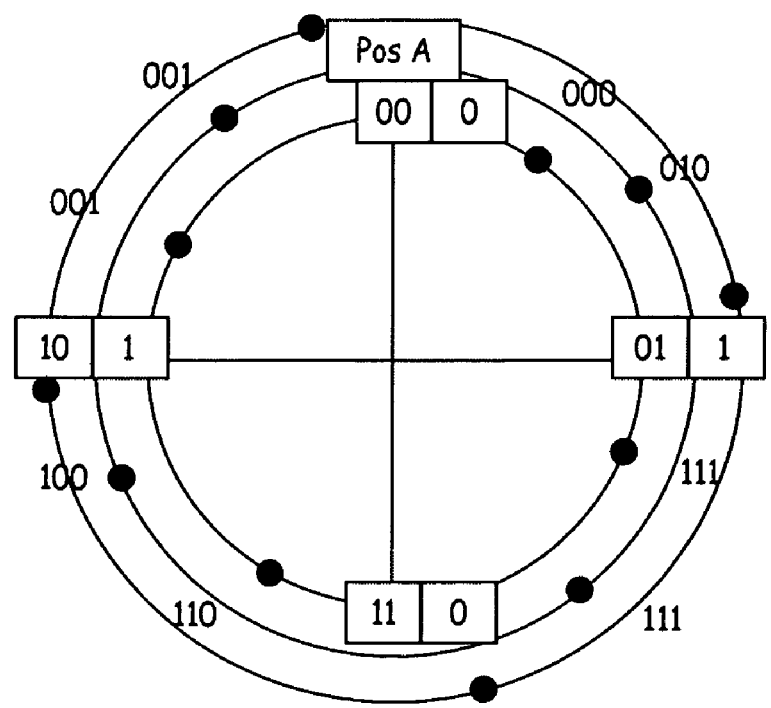
FIG. 7 is a schematic representation of the angle-dependent switching procedures of an exemplary realization of the codes shown in FIG. 6.

FIG. 7 schematically shows a diagram of a mechanical realization of the coding shown in FIG. 6, wherein the points indicated on the circles define the change in state of the respective bit. The innermost circle is assigned to the first bit, while the outer circle is assigned to the last bit which is used as a reference bit. The realization shown in FIG. 7 is particularly suitable for a dosing device which can only be rotated in one direction, since the reference bit changes immediately before and preferably at the same time as a new position is reached, such that the previously occurring changes in the first two bits have been stably performed.

Figure 8:
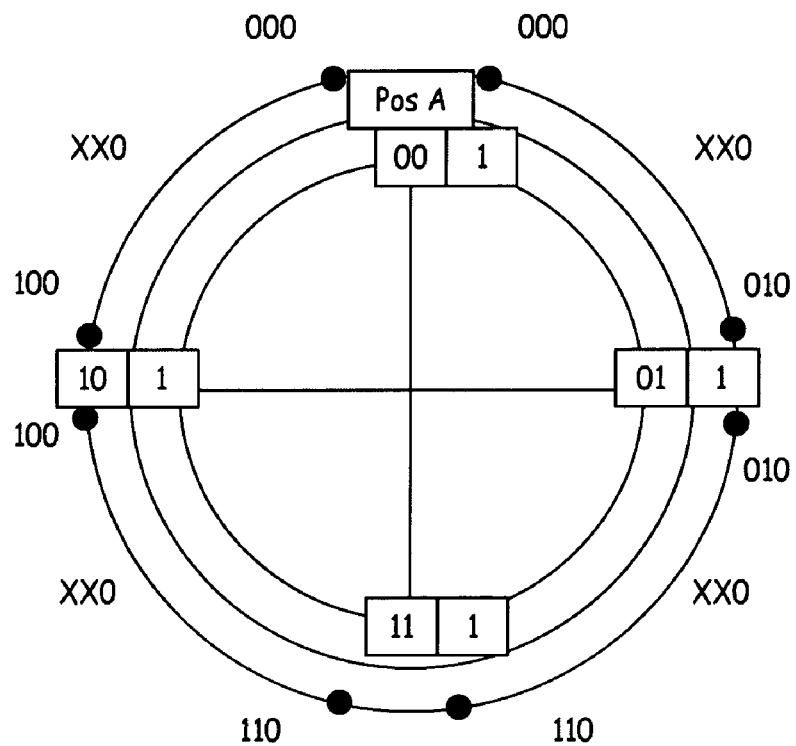
FIG. 8 depicts an exemplary two-bit coding scheme comprising a reference bit in accordance with one embodiment of the present invention for defining measuring positions.

FIG. 8 schematically shows an example of a mechanical realization of another embodiment of the invention, wherein the reference bit only assumes the value "1" at the particular rotational positions offset from each other by 90°. Between the defined rotational positions, the reference bit has the value "0", such that intermediate states of the two bits used to code the rotational position are not detected. The coding scheme shown in FIG. 8 can be realized using the device shown by way of example in FIGS. 1 to 3.

Figure 9:
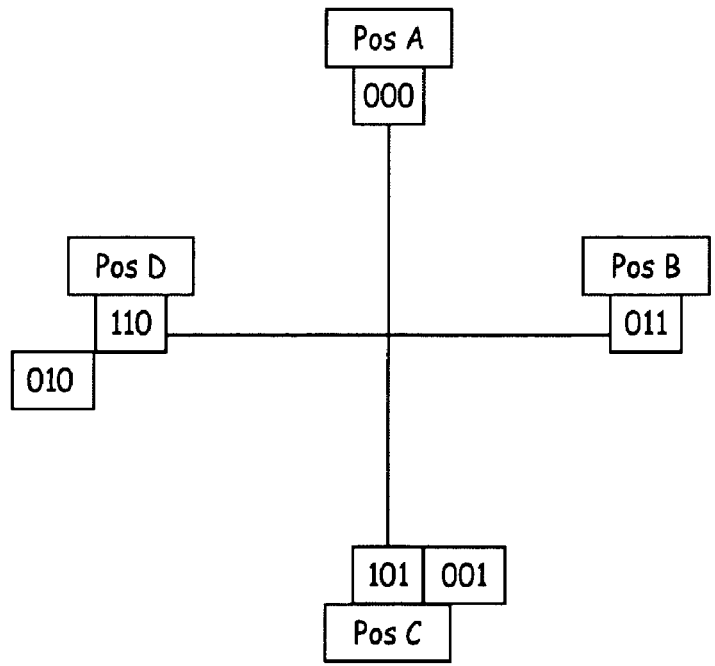
FIG. 9 depicts an exemplary non-separable coding using a three-bit code.

FIG. 9 shows four states, Position A to Position D, being coded, wherein neighbouring codes differ in each case by a change of two bits. If the first bit erroneously remains at the value "0", the change from Position B to Position C, for example, is recognized since the second bit is changed, and an error is outputted since the code "001" is invalid. In a subsequent transition to Position D, the code "010" is generated, such that an error can also be indicated here.

Figure 10:
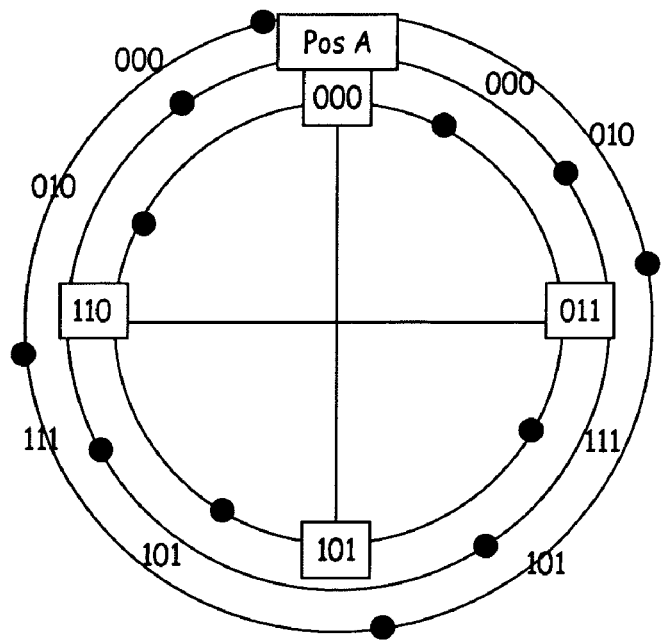
FIG. 10 is a functional diagram of a mechanical implementation of the coding shown in FIG. 9.

FIG. 10 schematically shows an exemplary implementation of the code shown in FIG. 9, comprising exemplary angle-dependent positions of the change in bit. This coding scheme can be used, in conjunction with a reference element in accordance with one embodiment of the invention, to generate a reference bit as shown, for example, in FIG. 8.

Figure 11:
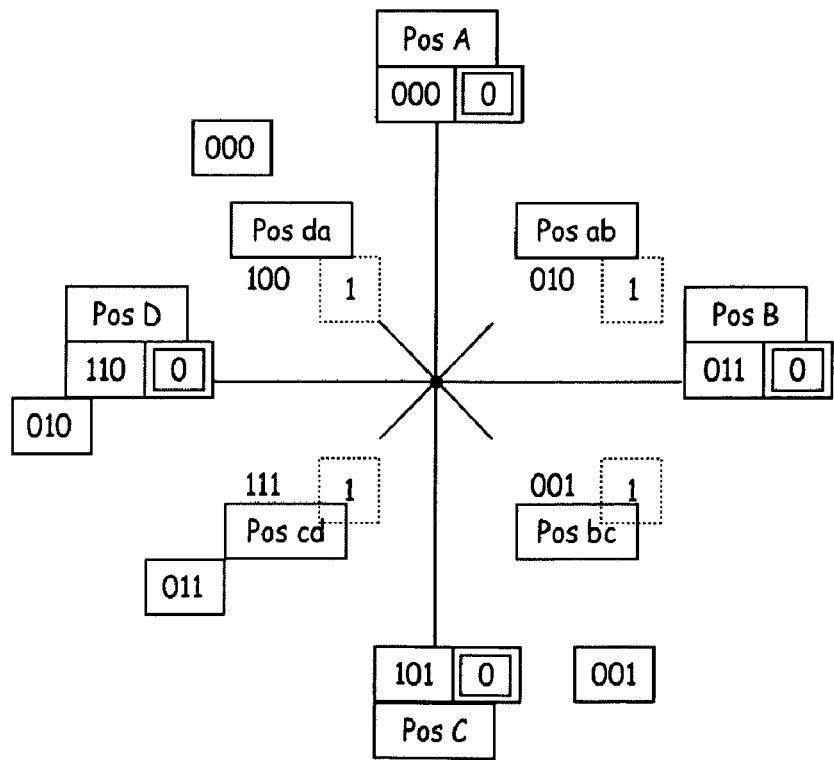
FIG. 11 depicts a three-bit coding scheme comprising an additional reference bit.

FIG. 11 shows a Gray coding of four positions A to D which are separated from each other by four intermediate states. The last bit is a reference bit and assumes the value "1" in intermediate positions, while it assumes the value "0" at the defined positions A to D. If, for example, the first bit is erroneously set to the value "0", then a transition from the intermediate position bc to the position C can be recognized due to the change in the last reference bit, even though the positional coding "001" is not changed. If another transition to the position cd occurs, the positional coding "011" cannot be erroneously interpreted as a correct code assigned to the position B, because the reference bit "1" of the intermediate state does not match the reference bit "0" of the defined state, such that this error can be clearly recognized.

Figure 12:
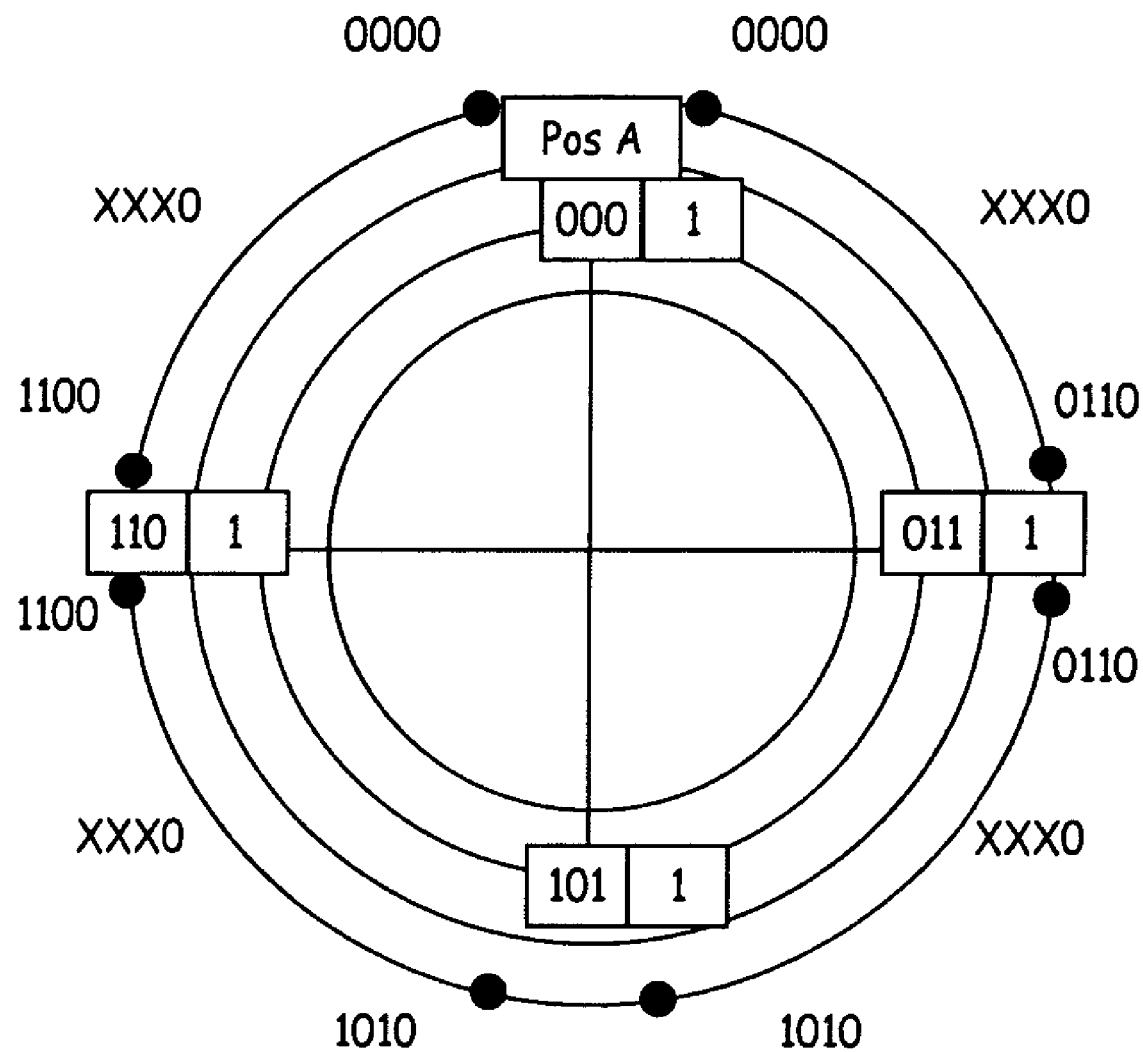
FIG. 12 depicts a scheme for mechanically realizing the coding shown in FIG. 11.

FIG. 12 schematically shows a mechanical implementation of the example shown in FIG. 11, wherein the reference bit is only set to the value "1" in the four defined positions shown by way of example and is set to the value "0" immediately before and after the defined positions. Because the code gap in this exemplary embodiment is 2, every change in an individual bit will be recognized as an invalid code and, thus, as an error.

Figure 13:
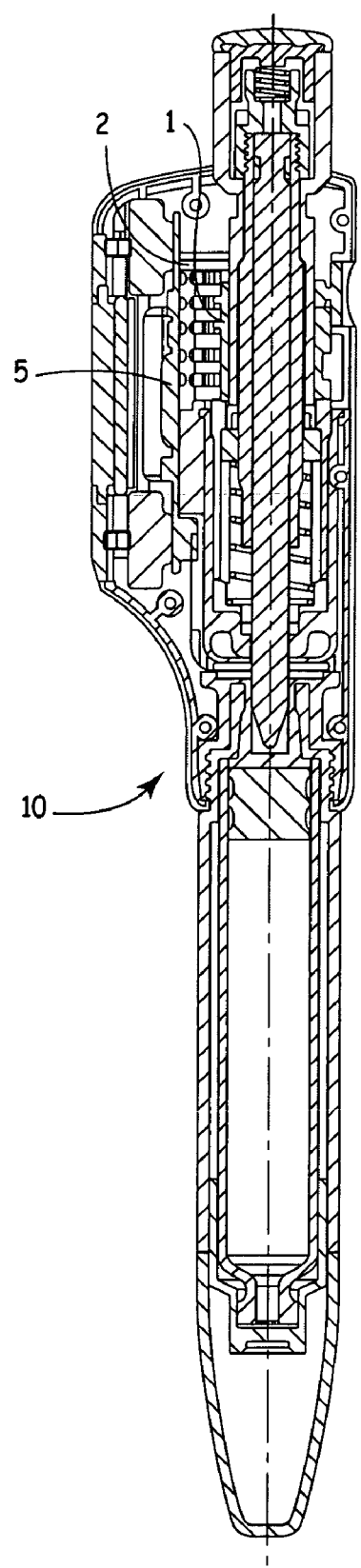
FIG. 13 depicts an injection apparatus comprising a coding and reference element in accordance with one embodiment of the present invention.

FIG. 13 shows, by way of example, an injection apparatus 10 in accordance with one embodiment of the present invention, wherein the injection apparatus comprises a cam shaft 1 and a switching and electronics element 2 for generating and ascertaining a code using a reference element.

In the foregoing description, embodiments of the present invention, including preferred embodiments, have been presented for the purpose of illustration and description. The embodiments were chosen and described to provide the best illustration of the principals of the devices and methods of the present invention and their practical use and implementation, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection or infusion device for dosing or dispensing an injectable substance in doses or selected amounts comprising:
at least one rotating element having at least one partial element disposed thereon for producing a coding related to a rotational position of the rotating element,
at least one reading element for reading the coding produced by the at least one partial element during a rotational dose setting movement, and
a reference element for generating a reference signal in a rotational position of the at least one rotating element,
whereby the rotational position of the at least one rotating element is identified by the reading element reading the coding only when the reference signal is generated.

2. The device according to claim 1, wherein the reference signal is generated at pre-set rotational positions or changes in rotational position of the rotating element.

3. An injection or infusion device for dosing a substance, comprising:
at least one rotating element having at least one partial element disposed thereon for producing a coding related to a rotational position of the rotating element; and
at least one reading element assigned to the rotating element, wherein a rotational position of the rotating element can be recognized by the reading element reading the coding produced by the at least one partial element during a rotational dose setting operation, and
at least one reference element which only generates a reference signal at pre-set rotational positions or changes in rotational position of the at least one rotating element,
wherein the rotational position of the rotating element is recognized by the reading element reading the coding during the dose setting operation when the reference signal is generated.

4. The device as set forth in claim 3, wherein the reference element is formed such that a reference signal can be generated in at least two pre-set rotational positions.

5. The device as set forth in claim 4, wherein the reference element is formed such that a reference signal can be generated from at least two to more than eight pre-set rotational positions.

6. The device as set forth in claim 4, wherein the reference element is formed such that a reference signal can be generated when the rotational position deviates from a pre-set position by one of from 0° to 30°, or 0° to 10° or 0° to 1°.

7. The device as set forth in claim 3, further comprising a power-consuming element, wherein the power-consuming element can be switched on and/or off by the reference signal.

8. The device as set forth in claim 3, wherein the at least one reading element produces a coding signal based at least in part on the coding, and wherein the coding and/or the reference signals are produced by mechanical elements.

9. The device as set forth in claim 3, wherein the at least one reading element produces a coding signal based at least in part on the coding, and wherein the coding and/or the reference signals are produced by optical elements.

10. The device as set forth in claim 3, further comprising at least one of an indicating element and a reset switch.

11. An injection or infusion device comprising:
at least one rotating element,
at least one partial element disposed on the at least one rotating element for producing a coding related to a rotational position of the rotating element,
at least one reading element for setting an amount of product to be dispensed in response to the reading element reading the coding produced by the at least one partial element, and
a reference element for generating a reference signal at a rotational position of the at least one rotating element,
whereby the rotational position of the rotating element can be identified by the reading element reading the coding only upon the reference element generating the reference signal.

12. The device as set forth in claim 3, wherein the reference element is formed of a series of protrusions offset with respect to each other in the circumferential direction and is disposed on the rotating element provided as a cam shaft.

13. The device as set forth in claim 12, wherein the reference signal is generated upon one of the series of protrusions contacting a switching pad of the reading element.

14. The device as set forth in claim 12, wherein spaces between the series of protrusions comprise intermediate states in which the cam shaft rotates but no reference signal is generated, wherein the reading element excludes the intermediate states or interprets the rotational positions as incorrect due to the absence of the generated reference signal.

15. The device as set forth in claim 12, wherein each of the series of reference element protrusions are substantially uniform in shape relative to each other and correspond to a pre-set position in which the reference signal is generated upon rotation of the cam shaft.

16. The device as set forth in claim 15, comprising at least two partial elements, wherein each of the at least two partial elements comprises a protruding element at positions offset or rotated with respect to each other, such that a multiple-digit code is generated by the at least two partial elements when the cam shaft is rotated to the pre-set positions.

17. The device as set forth in claim 16, wherein the at least two partial elements are arranged at different longitudinal positions along a longitudinal axis of the cam shaft and are longitudinally separated from the reference element protrusions.

18. An injection or infusion device for dosing or dispensing an injectable substance in doses or selected amounts comprising:
- at least one rotating element having at least one partial element disposed thereon for producing an indication related to a rotational position of the rotating element,
- at least one sensing element for sensing the indication produced by the at least one partial element during a rotational dose setting movement, and
- a reference element for generating a reference signal in a rotational position of the rotating element,
- whereby each of the at least one partial elements is axially offset with respect to the reference element, and
- whereby the rotational position of the rotating element is identified by the sensing element sensing the indication produced by the at least one partial element only when the reference signal is generated.

19. An injection or infusion device for dosing or dispensing an injectable substance in doses or selected amounts comprising:
- at least one rotating element having at least two partial elements disposed thereon for producing a coding signal related to a rotational position of the rotating element, whereby a first partial element is provided as a portion of the rotating element having a first cross section, and a second partial element is provided as a portion of the rotating element having a second cross section which is different than the first cross section,
- at least one sensing element for sensing rotation of the partial elements during a rotational dose setting movement, and
- a reference element for generating a reference signal in a rotational position of the rotating element,
- whereby the rotational position of the rotating element is identified by the sensing element sensing the coding produced by the partial elements only when the reference signal is generated.

* * * * *

UNITED STATES PATENT AND TRADEMARK OFFICE
CERTIFICATE OF CORRECTION

PATENT NO.         : 8,128,604 B2
APPLICATION NO.    : 11/009387
DATED              : March 6, 2012
INVENTOR(S)        : Julian Yeandel et al.

Page 1 of 1

It is certified that error appears in the above-identified patent and that said Letters Patent is hereby corrected as shown below:

SPECIFICATION

| Column | Line | PTO | Should Read |
|---|---|---|---|
| 3 | 13 | "rotation of 0°, 0°, 180° | -- rotation of 0°, 90°, 180° -- |
| 6 | 8 | "which differnet codes | -- which different codes -- |
| 6 | 12 | "in the order sections of BB | -- in the order sections BB -- |

Signed and Sealed this
First Day of May, 2012

David J. Kappos
*Director of the United States Patent and Trademark Office*